US011975088B2

(12) United States Patent
O'Connor et al.

(10) Patent No.: US 11,975,088 B2
(45) Date of Patent: May 7, 2024

(54) PERSONAL CARE COMPOSITION

(71) Applicants: Dow Global Technologies LLC, Midland, MI (US); Rohm and Haas Company, Collegeville, PA (US)

(72) Inventors: Ying O'Connor, Coatesville, PA (US); Fanwen Zeng, Audubon, PA (US); Lyndsay M. Leal, Spring City, PA (US); Peilin Yang, Pearland, TX (US); Asghar A. Peera, Royersford, PA (US); Sokhomari S. Suon, Ardmore, PA (US); Inna Shulman, Langhorne, PA (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 242 days.

(21) Appl. No.: 17/261,738

(22) PCT Filed: Aug. 22, 2019

(86) PCT No.: PCT/US2019/047643
§ 371 (c)(1),
(2) Date: Jan. 20, 2021

(87) PCT Pub. No.: WO2020/046695
PCT Pub. Date: Mar. 5, 2020

(65) Prior Publication Data
US 2021/0267863 A1    Sep. 2, 2021

Related U.S. Application Data

(60) Provisional application No. 62/725,304, filed on Aug. 31, 2018.

(51) Int. Cl.
*A61K 8/41* (2006.01)
*A61K 8/46* (2006.01)
*A61K 8/81* (2006.01)
*A61K 8/92* (2006.01)
*A61Q 19/10* (2006.01)

(52) U.S. Cl.
CPC .............. *A61K 8/416* (2013.01); *A61K 8/463* (2013.01); *A61K 8/8158* (2013.01); *A61K 8/922* (2013.01); *A61Q 19/10* (2013.01); *A61K 2800/5426* (2013.01); *A61K 2800/596* (2013.01)

(58) Field of Classification Search
CPC ................................ A61K 8/416; A61K 8/463
See application file for complete search history.

(56) References Cited

U.S. PATENT DOCUMENTS

| 7,723,453 | B2 | 5/2010 | Carnali et al. |
| 8,287,657 | B2 | 10/2012 | Song et al. |
| 2010/0226868 | A1 | 9/2010 | Gamez-Garcia et al. |
| 2010/0247472 | A1 | 9/2010 | Sau |

FOREIGN PATENT DOCUMENTS

| WO | 2010111576 | 9/2010 | |
| WO | 2012004126 | 1/2012 | |
| WO | WO-2016085706 A1 * | 6/2016 | ........... A61K 8/8158 |

OTHER PUBLICATIONS

Healthyandnaturalworld.com (https://www.healthyandnaturalworld.com/best-natural-oils-for-hair/#:~: text=The%20Best%20Natural%20Oils%20for%20Your%20Hair%201, . . . %208%20Pomegranate%20Seed%20Oil%20 . . . %20More%20items) (Year: 2022).*
Archive.org (https://web.archive.org/web/20161201000000/https://www.healthyandnaturalworld.com/best-natural-oils-for-hair/) (Year: 2016).*
Healthyandnaturalworld.com (https://www.healthyandnaturalworld.com/best-natural-oils-for-hair/#:~: text=The%20Best%20Natural%20Oils%20for%20Your%20Hair%201, . . . %208%20Pomegranate%20Seed%20Oil%20 . . . %20More%20items) (Year: 2022) (Year: 2022).*
Archive.org (https://web.archive.org/web/20161201000000/https://www.healthyandnaturalworld.com/best-natural-oils-for-hair/) (Year: 2016) (Year: 2016).*
Sibilia., "A Guide to Materials Characterization and Chemical Analysis." 1988, p. 81-84.

* cited by examiner

*Primary Examiner* — Andrew S Rosenthal
*Assistant Examiner* — Danielle Kim
(74) *Attorney, Agent, or Firm* — Thomas S. Deibert

(57) ABSTRACT

A personal care composition is provided, comprising: a vehicle; a cosmetically acceptable oil; and a cationic polymer comprising structural units of acrylamide monomer; structural units of N,N-dimethyl acrylamide monomer; and structural units of monoethylenically unsaturated monocationic monomer; wherein the cationic polymer comprises <10 mol % structural units of multiethylenically unsaturated cationic monomer; wherein the cationic polymer comprises <30 wt % structural units of ester containing monomers; wherein the cationic polymer comprises <1 mol % structural units of ethylenically unsaturated monomers containing a moiety selected from the group consisting of epoxy, anhydride, imide, lactone, carboxylic acid, sulfonic acid and isocyanate; wherein the cationic polymer comprises <0.1 mol % structural units of a reactive siloxane; and wherein the personal care composition comprises <0.05 wt % water soluble, organic, ampholytic polymer conditioning agent. Also provided is a method of using a personal care composition.

20 Claims, No Drawings

PERSONAL CARE COMPOSITION

The present invention relates to a personal care composition. In particular, the present invention relates to a personal care composition containing: a vehicle; a cosmetically acceptable oil; and a cationic polymer comprising structural units of acrylamide monomer; structural units of N,N-dimethyl acrylamide monomer; and structural units of a monoethylenically unsaturated monocationic monomer; wherein the cationic polymer comprises <10 mol % of structural units of multiethylenically unsaturated cationic monomer; wherein the cationic polymer comprises <30 wt % of structural units of ester containing monomers; wherein the cationic polymer comprises <1 mol % of structural units of ethylenically unsaturated monomers containing a moiety selected from the group consisting of an epoxy, an anhydride, an imide, a lactone, a carboxylic acid, a sulfonic acid and an isocyanate; wherein the cationic polymer comprises <0.1 mol % of structural units of a reactive siloxane; and wherein the personal care composition comprises <0.05 wt % of water soluble, organic, ampholytic polymer conditioning agent.

Deposition of moisturizers is of particular interest for various personal care compositions. In particular, there is interest for personal care cleansers (e.g., body wash, face wash, hand wash, soap, shampoo) that provide moisturizing benefits in addition to cleaning benefits.

Skin cleansing has become an ubiquitous component of personal hygiene. Cleansing of the skin facilitates the removal of dirt, germs and other things that are perceived as harmful to the skin or the individual. Cleansing formulations typically including a surfactant to promote the removal of materials deposited on the skin. Unfortunately, the cleansing formulations remove both undesirable and desirable materials from the skin. For example, cleansing formulations frequently undesirably remove oils from the skin, which oils operate to protect the skin from loss of moisture. Removal of too much oil from the skin may leave the skin vulnerable to becoming dry. One solution to this skin drying concern is the selection of mild surfactants. Another approach is to incorporate additives that help replace the oils removed through deposition; however, this approach has proven difficult in implementation, particularly in rinse off applications.

An approach to enhancing the deposition of materials on the skin is disclosed in United States Patent Application Publication No. 20100247472 to Sau. Sau disclose an aqueous personal care composition comprising a conditioner and a polymer functionalized with an amino group, wherein the amino group is pendant and the polymer functionalized with an amino group has the following structure:

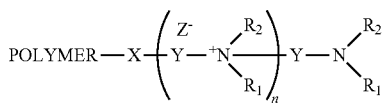

and, wherein the polymer comprises a natural, semisynthetic or synthetic polymer; comprises an oxygen, nitrogen or sulfur atom, or a polyalkylene oxide group; Y comprises a bivalent polyalkylene or substituted bivalent polyalkylene moiety; $R_1$ and $R_2$ may be the same or different and comprise hydrogen, $C_{1-20}$ alkyl, $C_{1-20}$ aryl or $C_{1-20}$ alkyl(aryl) group; n comprises an integer between 0 and 10; $Z^-$ comprises a counter anion, and wherein the conditioner is selected from the group consisting of cationic surfactants, cationic polymers, nucleic acids, lipids, silicones, hydrocarbon oil, fatty esters and combinations thereof.

While conventionally used deposition aids such as soluble cationic modified celluloses (e.g., PQ-10), guar hydroxypropyl triammonium chloride and other cationic polymers (e.g., PQ-6, PQ-7) provide a certain level of oil deposition in personal care cleansers; they nevertheless exhibit low efficiency necessitating a relatively high oil incorporation into the personal care cleanser formulation to facilitate desired skin moisturization. Such high oil levels, however, detrimentally effect the foam/lathery in use consumer feel of the formulation.

Accordingly, there remains a need for personal care compositions that facilitate moisturization while maintaining desirable in use consumer feel.

The present invention provides a personal care composition, comprising: a vehicle; a cosmetically acceptable oil; and a cationic polymer comprising: (a) 1 to 98 wt % of structural units of acrylamide monomer; (b) 1 to 98 wt % of structural units of N,N-dimethyl acrylamide monomer; (c) 1 to <30 wt % of structural units of monoethylenically unsaturated monocationic monomer of formula (I)

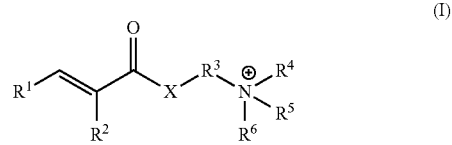

wherein $R^1$ is a —H or a —$CH_3$ group; wherein $R^2$ is a —H or a —$CH_3$ group; wherein X is an —O— or a —N—; wherein $R^3$ is a —$C_{1-4}$ alkylene; wherein $R^4$, $R^5$ and $R^6$ are each independently a —H or a $C_{1-30}$ alkyl group; with the proviso that $R^4$ and $R^5$ are each a —H or a —$CH_3$ group and $R^6$ is a —$C_{2-30}$ alkyl group in 1 to 100 mol % of the structural units of unsaturated monomer of formula (I); wherein the cationic polymer comprises >65 wt % of structural units of (a) and (b) combined; wherein the cationic polymer comprises <10 mol % of structural units of multi-ethylenically unsaturated cationic monomer; wherein the cationic polymer comprises <30 wt % of structural units of ester containing monomers; wherein the cationic polymer comprises <1 mol % of structural units of ethylenically unsaturated monomers containing a moiety selected from the group consisting of an epoxy, an anhydride, an imide, a lactone, a carboxylic acid, a sulfonic acid and an isocyanate; wherein the cationic polymer comprises <0.1 mol % of structural units of a reactive siloxane; and wherein the personal care composition comprises <0.05 wt % of water soluble, organic, ampholytic polymer conditioning agent.

The present invention provides a personal care composition, comprising: a vehicle; a cosmetically acceptable oil; and a cationic polymer comprising: (a) 1 to 98 wt % of structural units of acrylamide monomer; (b) 1 to 98 wt % of structural units of N,N-dimethyl acrylamide monomer; (c) 1 to <30 wt % of structural units of monoethylenically unsaturated monocationic monomer of formula (II)

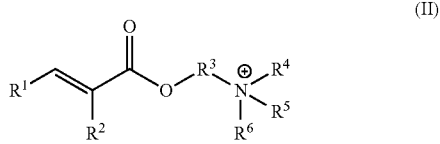

wherein $R^1$ is a —H or a —CH$_3$ group; wherein $R^2$ is a —H or a —CH$_3$ group; wherein $R^3$ is a —C$_{1-4}$ alkylene; wherein $R^4$, $R^5$ and $R^6$ are each independently a —H or a C$_{1-30}$ alkyl group; with the proviso that $R^4$ and $R^5$ are each a —H or a —CH$_3$ group and $R^6$ is a —C$_{2-30}$ alkyl group in 1 to 100 mol % of the structural units of unsaturated monomer of formula (I); wherein the cationic polymer comprises >65 wt % of structural units of (a) and (b) combined; wherein the cationic polymer comprises <10 mol % of structural units of multi-ethylenically unsaturated cationic monomer; wherein the cationic polymer comprises <30 wt % of structural units of ester containing monomers; wherein the cationic polymer comprises <1 mol % of structural units of ethylenically unsaturated monomers containing a moiety selected from the group consisting of an epoxy, an anhydride, an imide, a lactone, a carboxylic acid, a sulfonic acid and an isocyanate; wherein the cationic polymer comprises <0.1 mol % of structural units of a reactive siloxane; and wherein the personal care composition comprises <0.05 wt % of water soluble, organic, ampholytic polymer conditioning agent.

The present invention provides a method of using a personal care composition, comprising: providing a personal care composition of the present invention; and applying the personal care composition to at least one of skin and hair.

DETAILED DESCRIPTION

We have surprisingly found that a cationic polymer comprising structural units of acrylamide monomer; structural units of N,N-dimethyl acrylamide monomer; and structural units of a monoethylenically unsaturated monocationic monomer; wherein the cationic polymer comprises <10 mol % of structural units of multiethylenically unsaturated cationic monomer; wherein the cationic polymer comprises <30 wt % of structural units of ester containing monomers; wherein the cationic polymer comprises <1 mol % of structural units of ethylenically unsaturated monomers containing a moiety selected from the group consisting of an epoxy, an anhydride, an imide, a lactone, a carboxylic acid, a sulfonic acid and an isocyanate; wherein the cationic polymer comprises <0.1 mol % of structural units of a reactive siloxane; and wherein the personal care composition comprises <0.05 wt % of water soluble, organic, ampholytic polymer conditioning agent; provides excellent oil deposition efficiency such that moisturization may be provided while maintaining desirable in use consumer feel.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and poly(ethylene oxide) standards. GPC techniques are discussed in detail in Modem Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p81-84. Molecular weights are reported herein in units of Daltons, or equivalently, g/mol.

The term "cosmetically acceptable" as used herein and in the appended claims refers to ingredients typically used in personal care compositions, and is intended to underscore that materials that are toxic when present in the amounts typically found in personal care compositions are not contemplated as part of the present invention.

The term "structural units" as used herein and in the appended claims refers to the remnant of the indicated monomer; thus a structural unit of acrylamide monomer is illustrated:

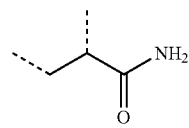

The term "structural units" as used herein and in the appended claims refers to the remnant of the indicated monomer; thus a structural unit of N,N-dimethyl acrylamide monomer is illustrated:

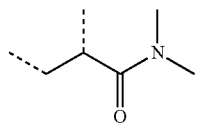

Preferably, the personal care composition of the present invention is selected from the group consisting of a body wash formulation, an exfoliating body wash formulation, a facial wash formulation, an exfoliating facial wash formulation, a liquid hand soap, a shampoo, a conditioning shampoo, a leave on hair conditioner, a rinse off hair conditioner, a hair coloring agent, a hair styling gel, a soap, a sunscreen, a sulfate-free cleansing formulation and a mild cleansing formulation. More preferably, the personal care composition of the present invention is selected from the group consisting of a body wash formulation, a facial wash formulation, leave on hair conditioner, rinse off hair conditioner, hair styling gel, sunscreen and a shampoo. Most preferably, the personal care composition of the present invention is a body wash formulation.

Preferably, the personal care composition of the present invention, comprises: a vehicle (preferably, wherein the vehicle comprises water; more preferably; wherein the vehicle is selected from the group consisting of water and an aqueous C$_{1-4}$ alcohol mixture; most preferably, wherein the vehicle is water); a cosmetically acceptable oil (preferably, wherein the cosmetically acceptable oil is selected from the group consisting of hydrocarbon oils (e.g., mineral oil, petroleum jelly, polyisobutene, hydrogenated polyisobutene, hydrogenated polydecene, polyisohexadecane); natural oils (e.g., caprylic and capric triglyceride, sunflower oil, soybean oil, coconut oil); silicone oils (e.g., polydimethylsiloxane); fragrance oils (e.g., limonene) and mixtures thereof; more preferably, wherein the cosmetically acceptable oil includes mineral oil; most preferably, wherein the cosmetically acceptable oil is mineral oil); and a cationic polymer comprising: (a) 1 to 98 wt % (preferably, 10 to 75 wt %; more preferably, 15 to 45 wt %; still more preferably, 20 to 40 wt %; most preferably, 25 to 35 wt %) of structural units of acrylamide monomer; (b) 1 to 98 wt % (preferably, 20 to 80 wt %; more preferably, 45 to 75 wt %; still more preferably, 50 to 70 wt %; most preferably, 55 to 65 wt %) of structural units of N,N-dimethyl acrylamide monomer; (c) 1 to <30 wt % (preferably, 5 to <25 wt %; more preferably, 7.5 to 20 wt %; still more preferably, 8 to 15 wt %; most preferably, 9 to 12 wt %) of structural units of a monoethylenically unsaturated monocationic monomer of formula (I) (preferably, formula (II))

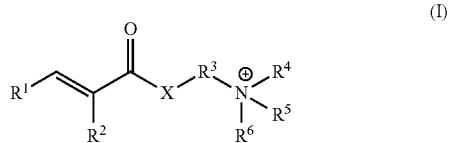

(I)

wherein $R^1$ is a —H or a —$CH_3$ group (preferably, a —H); wherein $R^2$ is a —H or a —$CH_3$ group (preferably, a —$CH_3$); wherein X is an —O— or a —N— (preferably, an —O—); wherein $R^3$ is a —$C_{1-4}$ alkylene (preferably, a —$C_2$ alkylene); wherein $R^4$, $R^5$ and $R^6$ are each independently a —H or a $C_{1-30}$ alkyl group; with the proviso that $R^4$ and $R^5$ are each a —H or a —$CH_3$ group (preferably, a —$CH_3$ group) and $R^6$ is a —$C_{2-30}$ alkyl group (preferably, a —$C_{4-22}$ alkyl group; more preferably, a —$C_{4-18}$ alkyl group; most preferably, a —$C_{5-12}$ alkyl group) in 1 to 100 mol % (preferably, 25 to 100 mol %; more preferably, 50 to 100 mol %; still more preferably, 75 to 100 mol %; yet still more preferably, 95 to 100 mol %; most preferably, 98 to 100 mol %) of the structural units of unsaturated monomer of formula (I); wherein the cationic polymer comprises >65 wt % of structural units of (a) and (b) combined; wherein the cationic polymer comprises <10 mol % of structural units of multiethylenically unsaturated cationic monomer; wherein the cationic polymer comprises <30 wt % of structural units of ester containing monomers; wherein the cationic polymer comprises <1 mol % (preferably, <0.1 mol %; more preferably, 0 to <0.01 mol %; still more preferably, 0 to <0.001 mol %; most preferably, 0 to <detectable limit) of structural units of ethylenically unsaturated monomers containing a moiety selected from the group consisting of an epoxy, an anhydride, an imide, a lactone, a carboxylic acid, a sulfonic acid and an isocyanate; wherein the cationic polymer comprises <0.1 mol % (preferably, 0 to <0.01 mol %; more preferably, 0 to <0.001 mol %; most preferably, 0 to <detectable limit) of structural units of a reactive siloxane; and wherein the personal care composition comprises <0.05 wt % of water soluble, organic, ampholytic polymer conditioning agent.

Preferably, the personal care composition of the present invention, comprises a vehicle, wherein the vehicle comprises water. More preferably, the personal care composition of the present invention, comprises: a vehicle, wherein the vehicle is selected from the group consisting of water and an aqueous $C_{1-4}$ alcohol mixture. Most preferably, the personal care composition of the present invention, comprises: a vehicle, wherein the vehicle is water.

Preferably, the personal care composition of the present invention, comprises: 25 to 99 wt % of a vehicle. Preferably, the personal care composition of the present invention, comprises: 30 to 95 wt % of a vehicle; wherein the vehicle comprises water. More preferably, the personal care composition of the present invention, comprises: 60 to 85 wt % of a vehicle; wherein the vehicle is selected from the group consisting of water and an aqueous $C_{1-4}$ alcohol mixture. Most preferably, the personal care composition of the present invention, comprises: 75 to 80 wt % of a vehicle; wherein the vehicle is water.

Preferably, the water used in the personal care composition of the present invention is at least one of distilled water and deionized water. More preferably, the water used in the personal care composition of the present invention is distilled and deionized.

Preferably, the personal care composition of the present invention, comprises: a cosmetically acceptable oil; wherein the cosmetically acceptable oil is selected from the group consisting of hydrocarbon oils (e.g., mineral oil, petroleum jelly, polyisobutene, hydrogenated polyisobutene, hydrogenated polydecene, polyisohexadecane); natural oils (e.g., caprylic and capric triglyceride, sunflower oil, soybean oil, coconut oil, argan oil); silicone oils (e.g., polydimethylsiloxane); fragrance oils (e.g., limonene) and mixtures thereof. More preferably, the personal care composition of the present invention, comprises: a cosmetically acceptable oil; wherein the cosmetically acceptable oil includes at least one of petroleum jelly, mineral oil and sunflower oil. Most preferably, the personal care composition of the present invention, comprises: a cosmetically acceptable oil; wherein the cosmetically acceptable oil is mineral oil.

Preferably, the personal care composition of the present invention, comprises: 0.5 to 40 wt % of a cosmetically acceptable oil. More preferably, the personal care composition of the present invention, comprises: 1 to 15 wt % of a cosmetically acceptable oil. Most preferably, the personal care composition of the present invention, comprises: 2.5 to 7.5 wt % of a cosmetically acceptable oil.

Preferably, the personal care composition of the present invention, comprises: a cationic polymer comprising: (a) 1 to 98 wt % (preferably, 10 to 75 wt %; more preferably, 15 to 45 wt %; still more preferably, 20 to 40 wt %; most preferably, 25 to 35 wt %) of structural units of acrylamide monomer; (b) 1 to 98 wt % (preferably, 20 to 80 wt %; more preferably, 45 to 75 wt %; still more preferably, 50 to 70 wt %; most preferably, 55 to 65 wt %) of structural units of N,N-dimethyl acrylamide monomer; (c) 1 to <30 wt % (preferably, 5 to <25 wt %; more preferably, 7.5 to 20 wt %; still more preferably, 8 to 15 wt %; most preferably, 9 to 12 wt %) of structural units of a monoethylenically unsaturated monocationic monomer of formula (I); wherein $R^1$ is a —H or a —$CH_3$ group (preferably, a —H); wherein $R^2$ is a —H or a —$CH_3$ group (preferably, a —$CH_3$); wherein X is an —O— or a —N— (preferably, an —O—); wherein $R^3$ is a —$C_{1-4}$ alkylene (preferably, a —$C_2$ alkylene); wherein $R^4$, $R^5$ and $R^6$ are each independently a —H or a $C_{1-30}$ alkyl group; with the proviso that $R^4$ and $R^5$ are each a —H or a —$CH_3$ group (preferably, a —$CH_3$ group) and $R^6$ is a —$C_{2-30}$ alkyl group (preferably, a —$C_{4-22}$ alkyl group; more preferably, a —$C_{4-8}$ alkyl group; most preferably, a —$C_{5-12}$ alkyl group) in 1 to 100 mol % (preferably, 25 to 100 mol %; more preferably, 50 to 100 mol %; still more preferably, 75 to 100 mol %; yet still more preferably, 95 to 100 mol %; most preferably, 98 to 100 mol %) of the structural units of unsaturated monomer of formula (I); wherein the cationic polymer comprises >65 wt % of structural units of (a) and (b) combined; wherein the cationic polymer comprises <10 mol % of structural units of multiethylenically unsaturated cationic monomer; wherein the cationic polymer comprises <30 wt % of structural units of ester containing monomers; wherein the cationic polymer comprises <1 mol % (preferably, <0.1 mol %; more preferably, 0 to <0.01 mol %; still more preferably, 0 to <0.001 mol %; most preferably, 0 to <detectable limit) of structural units of ethylenically unsaturated monomers containing a moiety selected from the group consisting of an epoxy, an anhydride, an imide, a lactone, a carboxylic acid, a sulfonic acid and an isocyanate; wherein the cationic polymer comprises <0.1 mol % (preferably, 0 to <0.01 mol %; more preferably, 0 to <0.001 mol %; most preferably, 0 to <detectable limit) of structural units of a reactive siloxane; and wherein the personal care composition comprises <0.05 wt % of water soluble, organic, ampholytic polymer conditioning agent.

Preferably, the personal care composition of the present invention, comprises: a cationic polymer comprising: (a) 1 to 98 wt % (preferably, 10 to 75 wt %; more preferably, 15 to 45 wt %; still more preferably, 20 to 40 wt %; most preferably, 25 to 35 wt %) of structural units of acrylamide monomer; (b) 1 to 98 wt % (preferably, 20 to 80 wt %; more preferably, 45 to 75 wt %; still more preferably, 50 to 70 wt %; most preferably, 55 to 65 wt %) of structural units of N,N-dimethyl acrylamide monomer; (c) 1 to <30 wt % (preferably, 5 to <25 wt %; more preferably, 7.5 to 20 wt %; still more preferably, 8 to 15 wt %; most preferably, 9 to 12 wt %) of structural units of a monoethylenically unsaturated monocationic monomer of formula (II)

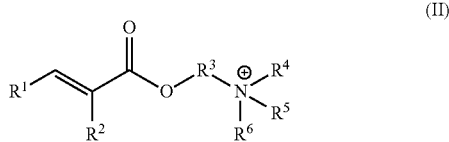

wherein $R^1$ is a —H or a —CH$_3$ group (preferably, a —H); wherein $R^2$ is a —H or a —CH$_3$ group (preferably, a —CH$_3$); wherein $R^3$ is a —C$_{1-4}$ alkylene (preferably, a —C$_2$ alkylene); wherein $R^4$, $R^5$ and $R^6$ are each independently a —H or a C$_{1-30}$ alkyl group; with the proviso that $R^4$ and $R^5$ are each a —H or a —CH$_3$ group (preferably, a —CH$_3$ group) and $R^6$ is a —C$_{2-30}$ alkyl group (preferably, a —C$_{4-22}$ alkyl group; more preferably, a —C$_{4-8}$ alkyl group; most preferably, a —C$_{5-12}$ alkyl group) in 1 to 100 mol % (preferably, 25 to 100 mol %; more preferably, 50 to 100 mol %; still more preferably, 75 to 100 mol %; yet still more preferably, 95 to 100 mol %; most preferably, 98 to 100 mol %) of the structural units of unsaturated monomer of formula (II); wherein the cationic polymer comprises >65 wt % of structural units of (a) and (b) combined; wherein the cationic polymer comprises <10 mol % of structural units of multiethylenically unsaturated cationic monomer; wherein the cationic polymer comprises <30 wt % of structural units of ester containing monomers; wherein the cationic polymer comprises <1 mol % (preferably, <0.1 mol %; more preferably, 0 to <0.01 mol %; still more preferably, 0 to <0.001 mol %; most preferably, 0 to <detectable limit) of structural units of ethylenically unsaturated monomers containing a moiety selected from the group consisting of an epoxy, an anhydride, an imide, a lactone, a carboxylic acid, a sulfonic acid and an isocyanate; wherein the cationic polymer comprises <0.1 mol % (preferably, 0 to <0.01 mol %; more preferably, 0 to <0.001 mol %; most preferably, 0 to <detectable limit) of structural units of a reactive siloxane; and wherein the personal care composition comprises <0.05 wt % of water soluble, organic, ampholytic polymer conditioning agent.

Preferably, the personal care composition of the present invention, comprises: 0.05 to 10 wt % of the cationic polymer. More preferably, the personal care composition of the present invention, comprises: 0.1 to 5 wt % of the cationic polymer. Still more preferably, the personal care composition, comprises: 0.2 to 2 wt % of the cationic polymer. Most preferably, the personal care composition, comprises: 0.25 to 1 wt % of the cationic polymer.

Preferably, the cationic polymer used in the personal care composition of the present invention has a weight average molecular weight of ≤500,000 g/mol (preferably, ≤400,000 g/mol; more preferably, ≤375,000 g/mol). Preferably, the cationic polymer used in the personal care composition of the present invention has a weight average molecular weight of ≥100,000/mol (preferably, ≥200,000 g/mol; more preferably, ≥250,000 g/mol).

Preferably, the cationic polymer used in the personal care composition of the present invention has a weight average molecular weight of 100,000 to 500,000 g/mol (preferably, 200,000 to 400,000 g/mol; more preferably, 250,000 to 375,000 g/mol). Preferably, the cationic polymer comprises <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties. More preferably, the cationic polymer comprises <0.1 mol % (preferably, 0 to <0.01 mol %; more preferably, 0 to <0.001 mol %; most preferably, 0 to <detectable limit) of structural units of a reactive siloxane, wherein the structural units of a reactive siloxane include Si—O moieties; wherein the reactive siloxane is a polymer which may comprise one or more functional moieties selected from the group consisting of amino, amido, alkoxy, hydroxy, polyether, carboxy, hydride, mercapto, sulfate phosphate, and/or quaternary ammonium moieties—these moieties may be attached directly to the siloxane backbone through a bivalent alkylene radical, (i.e., pendant) or may be part of the backbone.

Preferably, the personal care composition of the present invention, optionally, further comprises at least one additional ingredient selected from the group consisting of an antimicrobial agent; a personal care cleaning surfactant; a rheology modifier; a soap; a colorant; pH adjusting agent; an antioxidant (e.g., butylated hydroxytoluene); a humectant (e.g., glycerin, sorbitol, monoglycerides, lecithins, glycolipids, fatty alcohols, fatty acids, polysaccharides, sorbitan esters, polysorbates (e.g., Polysorbate 20, Polysorbate 40, Polysorbate 60, and Polysorbate 80), diols (e.g., propylene glycol), diol analogs, triols, triol analogs, cationic polymeric polyols); a wax; a foaming agent; an emulsifying agent; a colorant; a fragrance; a chelating agent; a preservative (e.g., benzoic acid, sorbic acid, phenoxyethanol); a bleaching agent; a lubricating agent; a sensory modifier; a sunscreen additive; a vitamin; a protein/amino acid; a plant extract; a natural ingredient; a bioactive agent; an anti-aging agent; a pigment; an acid; a penetrant; an antimicrobial; an anti-static agent; an anti-frizz agent; an antidandruff agent; a hair waving/straightening agent; a hair styling agent; an absorbent; a hard particle; a soft particle; a conditioning agent (e.g., guar hydroxypropyltrimonium chloride, PQ-10, PQ-7); a slip agent; an opacifier; a pearlizing agent; a salt and mixtures thereof. More preferably, the personal care composition of the present invention, optionally, further comprises at least one additional ingredient selected from the group consisting of at least one of an antimicrobial agent, a personal care cleaning surfactant, a rheology modifier, a soap, a colorant and a pH adjusting agent.

Preferably, the personal care composition of the present invention further comprises an antimicrobial agent. More preferably, the personal care composition of the present invention further comprises an antimicrobial agent, wherein the antimicrobial agent is selected from the group consisting of phenoxyethanol, benzoic acid, benzyl alcohol, sodium benzoate, DMDM hydantoin, 2-ethylhexyl glyceryl ether and isothiazolinone (e.g., methylchloroisothiazolinone, methylisothiazolinone). Still more preferably, the personal care composition of the present invention, further comprises an antimicrobial agent, wherein the antimicrobial agent is an isothiazolinone (more preferably, wherein the antimicrobial is selected from the group consisting of methylisothiazolinone, methylchloroisothiazolinone and mixtures thereof; most preferably, wherein the biocide is methylisothiazolinone). Most preferably, the personal care composition of the present invention, further comprises an antimicrobial agent, wherein the antimicrobial agent is an isothiazolinone (more preferably, wherein the antimicrobial agent is selected from the group consisting of methylisothiazolinone, methylchloroisothiazolinone and mixtures thereof; most preferably, wherein the antimicrobial agent is methylisothiazolinone); and wherein the personal care composition is a body wash formulation.

Preferably, the personal care composition of the present invention further comprises a personal care cleaning surfactant. More preferably, the personal care composition of the present invention further comprises a personal care cleaning surfactant, wherein the personal care cleaning surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof. Still more preferably, the personal care composition of the present invention further comprises a personal care cleaning surfactant; wherein the personal care composition is a body wash formulation and wherein the personal care cleaning surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof. Most preferably, the personal care composition of the present invention further comprises a personal care cleaning surfactant; wherein the personal care composition is a body wash formulation and wherein the personal care cleaning surfactant comprises a mixture of sodium laureth sulfate (SLES) and cocamidopropyl betaine.

Preferably, the personal care composition of the present invention further comprises 0.01 to 80 wt % (more preferably, 5 to 50 wt %; still more preferably, 7.5 to 35 wt %, most preferably, 10 to 20 wt %) of a personal care cleaning surfactant. More preferably, the personal care composition of the present invention further comprises 0.01 to 80 wt % (more preferably, 5 to 50 wt %; still more preferably, 7.5 to 35 wt %, most preferably, 10 to 20 wt %) of a personal care cleaning surfactant, wherein the personal care cleaning surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof. Still more preferably, the personal care composition of the present invention further comprises 0.01 to 80 wt % (more preferably, 5 to 50 wt %; still more preferably, 7.5 to 35 wt %, most preferably, 10 to 20 wt %) of a personal care cleaning surfactant; wherein the personal care composition is a body wash formulation and wherein the personal care cleaning surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof. Most preferably, the personal care composition of the present invention further comprises 0.01 to 80 wt % (more preferably, 5 to 50 wt %; still more preferably, 7.5 to 35 wt %, most preferably, 10 to 20 wt %) of a personal care cleaning surfactant; wherein the personal care composition is a body wash formulation and wherein the personal care cleaning surfactant comprises a mixture of sodium laureth sulfate (SLES) and cocamidopropyl betaine.

Preferably, the personal care composition of the present invention further comprises a soap. More preferably, the personal care composition of the present invention further comprises a soap, wherein the soap is selected from the group consisting of sodium stearate, sodium laurate, sodium tallowate, sodium palmitate, potassium stearate, potassium laurate, potassium tallowate, potassium palmitate and mixtures thereof. Still more preferably, the personal care composition of the present invention further comprises a soap, wherein the soap is selected from the group consisting of sodium stearate, sodium laurate, potassium stearate, potassium laurate and mixtures thereof. Yet more preferably, the personal care composition of the present invention further comprises a soap, wherein the soap is selected from the group consisting of sodium stearate, potassium stearate and mixtures thereof. Most preferably, the personal care composition of the present invention further comprises a soap, wherein the soap comprises sodium stearate.

Preferably, the personal care composition of the present invention, further comprises a soap, wherein the soap is selected from the group consisting of sodium stearate, sodium laurate, sodium tallowate, sodium palmitate, potassium stearate, potassium laurate, potassium tallowate, potassium palmitate and mixtures thereof (more preferably, wherein the soap is selected from the group consisting of sodium stearate, sodium laurate, potassium stearate, potassium laurate and mixtures thereof; still more preferably, wherein the soap is selected from the group consisting of sodium stearate, potassium stearate and mixtures thereof;

most preferably, wherein the soap is sodium stearate); and wherein the personal care composition is a body wash formulation.

Preferably, the personal care composition of the present invention further comprises a rheology modifier. More preferably, the personal care composition of the present invention further comprises a rheology modifier; wherein the rheology modifier is selected from the group consisting of sodium chloride, cellulose, xanthan gum, an acrylates copolymer and mixtures thereof. Still more preferably, the personal care composition of the present invention further comprises a rheology modifier; wherein the rheology modifier includes an acrylates copolymer; wherein the acrylates copolymer is an ionic acrylic based rheology modifier. Yet more preferably, the personal care composition of the present invention further comprises a rheology modifier; wherein the rheology modifier is an acrylates copolymer is an alkali-swellable anionic acrylic copolymer (e.g., Aculyn™ 33, Aculyn™ 22, Aculyn™28, Aculyn™88 rheology modifiers all available from The Dow Chemical Company). Most preferably, the personal care composition of the present invention further comprises a rheology modifier; wherein the personal care composition is a body wash formulation and wherein the rheology modifier is an alkali-swellable anionic acrylic copolymer (e.g., Aculyn™ 33, Aculyn™22, Aculyn™ 28, Aculyn™ 88 rheology modifiers all available from The Dow Chemical Company).

Preferably, the personal care composition of the present invention further comprises a pH adjusting agent. More preferably, the personal care composition of the present invention, further comprises a pH adjusting agent, wherein the personal care composition is a body wash formulation. Most preferably, the personal care composition of the present invention, further comprises a pH adjusting agent, wherein the personal care composition is a body wash formulation and wherein the body wash formulation has a pH of 4.5 to 9 (preferably, 5 to 8; most preferably, 6 to 7).

Preferably, the pH adjusting agent is selected from the group consisting of at least one of citric acid, lactic acid, hydrochloric acid, aminoethyl propanediol, triethanolamine, monoethanolamine, sodium hydroxide, potassium hydroxide, amino-2-methyl-1-propanol. More preferably, the pH adjusting agent is selected from the group consisting of at least one of citric acid, lactic acid, sodium hydroxide, potassium hydroxide, triethanolamine, amino-2-methyl-1-propanol. Still more preferably, the pH adjusting agent includes is triethanolamine. Most preferably, the pH adjusting agent is triethanolamine.

Preferably, the personal care composition of the present invention further comprises a colorant. More preferably, the personal care composition of the present invention, further comprises a colorant, wherein the personal care composition is a body wash formulation.

Preferably, the personal care composition of the present invention is a body wash formulation. More preferably, the personal care composition of the present invention is a body wash formulation, comprising: 25 to 99 wt % (preferably, 30 to 90 wt %; more preferably, 60 to 85 wt %; most preferably, 75 to 80 wt %) of a vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil. Still more preferably, the personal care composition of the present invention is a body wash formulation, comprising 25 to 99 wt % (preferably, 30 to 90 wt %; more preferably, 60 to 85 wt %; most preferably, 75 to 80 wt %) of a vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil; wherein the cosmetically acceptable oil is selected from the group consisting of hydrocarbon oils (e.g., mineral oil, petroleum jelly); natural oils (e.g., sunflower oil, soybean oil, coconut oil); silicone oils (e.g., polydimethylsiloxane); fragrance oils (e.g., limonene) and mixtures thereof. Yet more preferably, the personal care composition of the present invention is a body wash formulation, comprising 25 to 99 wt % (preferably, 30 to 90 wt %; more preferably, 60 to 85 wt %; most preferably, 75 to 80 wt %) of vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil; wherein the cosmetically acceptable oil is selected from the group consisting of at least one of mineral oil, petroleum jelly, sunflower oil, soybean oil, coconut oil, silicone oil and fragrance oil. Yet still more preferably, the personal care composition of the present invention is a body wash formulation, comprising 25 to 99 wt % (preferably, 30 to 90 wt %; more preferably, 60 to 85 wt %; most preferably, 75 to 80 wt %) of a vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil; wherein the cosmetically acceptable oil includes mineral oil. Most preferably, the personal care composition of the present invention is a body wash formulation, comprising 25 to 99 wt % (preferably, 30 to 90 wt %; more preferably, 60 to 85 wt %; most preferably, 75 to 80 wt %) of a vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil; wherein the cosmetically acceptable oil is mineral oil.

Preferably, the personal care composition of the present invention is a body wash formulation. More preferably, the personal care composition of the present invention is a body wash formulation, comprising: 25 to 99 wt % (preferably, 30 to 90 wt %; more preferably, 60 to 85 wt %; most preferably, 75 to 80 wt %) of a vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil; and 0.01 to 80 wt % (more preferably, 5 to 50 wt %; still more preferably, 7.5 to 35 wt %, most preferably, 10 to 20 wt %) of a personal care cleaning surfactant. Still more preferably, the personal care composition of the present invention is a body wash formulation, comprising 25 to 99 wt % (preferably, 30 to 90 wt %; more preferably, 60 to 85 wt %; most preferably, 75 to 80 wt %) of a vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil; wherein the cosmetically acceptable oil is selected from the group consisting of hydrocarbon oils (e.g., mineral oil, petroleum jelly); natural oils (e.g., sunflower oil, soybean oil, coconut oil); silicone oils (e.g., polydimethylsiloxane); fragrance oils (e.g., limonene) and mixtures thereof; and 0.01 to 80 wt % (more preferably, 5 to 50 wt %; still more preferably, 7.5 to 35 wt %, most preferably, 10 to 20 wt %) of a personal care cleaning surfactant, wherein the personal care cleaning surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof. Yet more preferably, the personal care composition of the present invention is a body wash formulation, comprising 25 to 99 wt % (preferably, 30 to 90 wt %; more preferably, 60 to 85 wt %; most preferably, 75 to 80 wt %) of a vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil; wherein the cosmetically acceptable oil is selected from the group consisting of at least one of mineral oil, petroleum jelly, sunflower oil, soybean oil, coconut oil, silicone oil and fragrance oil; and 0.01 to 80 wt % (more preferably, 5 to 50 wt %; still more preferably, 7.5 to 35 wt %, most preferably, 10 to 20 wt %) of a personal care cleaning surfactant; wherein the personal care composition is a body wash formulation and wherein the personal care cleaning surfactant is selected from the group consisting of alkyl polyglucosides (e.g., lauryl glucoside, coco-glucoside, decyl glucoside), glycinates (e.g., sodium cocoyl glycinate), betaines (e.g., alkyl betaines such as cetyl betaine and amido betaines such as cocamidopropyl betaine), taurates (e.g., sodium methyl cocoyl taurate), glutamates (e.g., sodium cocoyl glutamate), sarcosinates (e.g., sodium lauroyl sarcosinate), isethionates (e.g., sodium cocoyl isethionate, sodium lauroyl methyl isethionate), sulfoacetates (e.g., sodium lauryl sulfoacetate), alaninates (e.g., sodium cocoyl alaninate), amphoacetates (e.g., sodium cocoamphoacetate), sulfates (e.g., sodium laureth sulfate), sulfonates (e.g., sodium $C_{14-16}$ olefin sulfonate), succinates (e.g., disodium lauryl sulfosuccinate) and mixtures thereof. Yet still more preferably, the personal care composition of the present invention is a body wash formulation, comprising 25 to 99 wt % (preferably, 30 to 90 wt %; more preferably, 60 to 85 wt %; most preferably, 75 to 80 wt %) of a vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil; wherein the cosmetically acceptable oil includes mineral oil; and 0.01 to 80 wt % (more preferably, 5 to 50 wt %; still more preferably, 7.5 to 35 wt %, most preferably, 10 to 20 wt %) of a personal care cleaning surfactant; wherein the personal care composition is a body wash formulation and wherein the personal care cleaning surfactant comprises a mixture of sodium laureth sulfate (SLES) and cocamidopropyl betaine. Most preferably, the personal care composition of the present invention is a body wash formulation, comprising 25 to 99 wt % (preferably, 30 to 90 wt %; more preferably, 60 to 85 wt %; most preferably, 75 to 80 wt %) of a vehicle (preferably, water); 0.05 to 10 wt % (preferably, 0.1 to 5 wt %; more preferably, 0.2 to 2 wt %; most preferably, 0.25 to 1 wt %) of a cationic polymer of the present invention; 0.5 to 40 wt % (preferably, 1 to 15 wt %; more preferably, 2.5 to 7.5 wt %) of a cosmetically acceptable oil; wherein the cosmetically acceptable oil is mineral oil; and 0.01 to 80 wt % (more preferably, 5 to 50 wt %; still more preferably, 7.5 to 35 wt %, most preferably, 10 to 20 wt %) of a personal care cleaning surfactant; wherein the personal care composition is a body wash formulation and wherein the personal care cleaning surfactant comprises a mixture of sodium laureth sulfate (SLES) and cocamidopropyl betaine.

Preferably, the method of using a personal care composition of the present invention, comprises: providing a personal care composition of the present invention and applying the personal care composition to at least one of skin and hair. More preferably, the method of using a personal care composition of the present invention, further comprises: rinsing the personal care composition from the at least one of skin and hair with a rinse water. Most preferably, the method of using a personal care composition of the present invention, comprises: providing a personal care composition of the present invention; applying the personal care composition to a skin; and rinsing the personal care composition from the skin; wherein the personal care composition is a body wash formulation.

Some embodiments of the present invention will now be described in detail in the following Examples.

Examples S1-S5: Synthesis of Cationic Polymer

A cationic polymer was prepared in a one-liter round bottom flask equipped with a mechanical overhead stirrer, a heating mantle, a thermocouple, a condenser and inlets for addition of monomer, initiator and nitrogen. The flask was charged with 224 g of deionized water. The stirrer was energized, a nitrogen purge through the vapor space in the flask was started and the temperature set point for the heating mantel was set at 75° C.

In a 500 mL graduated cylinder was prepared a monomer mixture by adding 139.0 g of deionized water; A g of a 50 wt % solution of acrylamide in deionized water; B g of N,N-dimethyl acrylamide; C g of a 70 wt % solution of 3-acrylamidopropyltrimethyl ammonium chloride in deionized water; and D g of a monoethylenically unsaturated monomer of formula

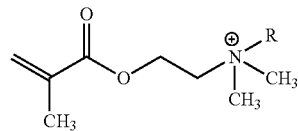

with R as noted in TABLE 1. The contents of the graduated cylinder were mixed until uniform.

In a separate container was prepared a co-feed catalyst by adding 2.25 g of Vazo-56 and 19.35 g of deionized water.

When the contents of the flask reached 75° C., the co-feed catalyst was added to the flask at a rate of 0.16 g/min for 137 minutes. Two minutes following the start of the co-feed catalyst, the monomer mixture was added to the flask at a rate of 2.79 g/min over a period of 120 minutes.

Following completion of the feeds to the flask, 15.3 g of deionized water was added as a rinse and the flask contents were held for 30 minutes at 75° C. During this hold, a chase promoter of a 4.3 g solution of 0.15 wt % iron sulfate heptahydrate with versene was prepared. A chase activator solution of 0.64 g of isoascorbic acid dissolved in 8.91 g of deionized water was prepared. A chase catalyst solution of 1 g of 70 wt % tert-butyl hydroperoxide in 8.6 g of deionized water was prepared. Following the 30 minute hold, the heating mantle was removed and the flask contents were allowed to cool. When the flask contents reached 70° C., the chase promoter solution was added as a shot to the flask contents. The chase activator solution and the chase catalyst solution were then added to the flask contents separately by syringe pump at a rate of 0.32 g/minute over 30 minutes.

When cooled to 25° C., the flask contents were transferred to a plastic jar and characterized for solids. The results are provided in TABLE 1.

TABLE 1

| Ex. | A (g) | B (g) | C (g) | D (g) | R | Solids (wt %) |
|---|---|---|---|---|---|---|
| S1 | 91.0 | 89.4 | 20 | 0 | — | 25.86 |
| S2 | 91.0 | 89.4 | 10 | 7.5 | —$C_{12}$ alkyl | 24.92 |
| S3 | 91.0 | 89.4 | 0 | 15.0 | —$C_{12}$ alkyl | 25.75 |
| S4 | 91.0 | 89.4 | 0 | 15.0 | —$C_6$ alkyl | 24.49 |
| S5 | 91.0 | 89.4 | 0 | 15.0 | —$C_{16}$ alkyl | 15.51 |

Comparative Examples C1-C2 and Examples 1-4: Personal Care Composition

Personal care compositions were prepared in each of Comparative Examples C1-C2 and Examples 1-4 by combining the components in the amounts listed in TABLE 2.

TABLE 2

| Component | Example (wt %) | | | | | |
|---|---|---|---|---|---|---|
| | C1 | C2 | 1 | 2 | 3 | 4 |
| Guar hydroxypropyltrimonium chloride[1] | 0.4 | — | — | — | — | — |
| Sodium laureth sulfate[2] | 48.0 | 48.0 | 48.0 | 48.0 | 48.0 | 48.0 |
| Cocamidopropyl betaine[3] | 8.5 | 8.5 | 8.5 | 8.5 | 8.5 | 8.5 |
| Mineral oil[4] | 5.0 | 5.0 | 5.0 | 5.0 | 5.0 | 5.0 |
| Product of Synthesis S1 | — | 1.55 | — | — | — | — |
| Product of Synthesis S2 | — | — | 1.61 | — | — | — |
| Product of Synthesis S3 | — | — | — | 1.55 | — | — |
| Product of Synthesis S4 | — | — | — | — | 1.63 | — |
| Product of Synthesis S5 | — | — | — | — | — | 2.58 |
| Acrylates copolymer[5] | 7.14 | 11.4 | 11.4 | 11.4 | 12.6 | 11.9 |
| Preservative[6] | 0.8 | 0.8 | 0.8 | 0.8 | 0.8 | 0.8 |
| Water | q.s. 100 | q.s. 100 | q.s. 100 | q.s. 100 | q.s. 100 | q.s. 100 |

[1]EcoSmooth ™ 100 conditional polymer available from The Dow Chemical Company
[2]Steol CS-130 sodium laureth sulfate (aq. 25 wt %) available from Stepan Company
[3]Amphosol CA cocamidopropyl betaine (aq. 30 wt %) available from Stepan Company
[4]Lilac ® highly refined mineral oil from Sonneborn, LLC
[5]Aculyn ™ 33 acrylates copolymer available from The Dow Chemical Company
[6]Glydant ® DMDM hydantion available from Lonza Performance Testing The personal care composition from each of Comparative Examples C1-C2 and Examples 1-4 were titrated to a pH of 6.5 with triethanolamine. The final compositions were then applied to a Vitro-Skin® advanced testing substrate (available from IMS Inc.) using a cot covered finger. The treated substrates were then rinsed with deionized water and evaluated for deposition of oil onto the substrate. Eight replicate Vitro-Skin® advanced testing substrate samples were prepared for each of the personal care compositions. The following procedure was used: (a) Vitro-Skin® advanced testing substrate was cut into 4 cm×4 cm pieces; (b) Each test substrate was weighted; (c) Using a 1 mL HSW syringe (Henke Saas Wolf GmbH), a 0.2 mL sample of the personal care composition was deposited onto the rough side of the test substrate; (d) Using a cot covered finger, the deposited personal care composition was then gently rubbed on the substrate for about 15 seconds; (e) Each test substrate was weighted again following treatment with the personal care composition; (f) Each treated substrate was set aside for 20 seconds before rinsing with water; (g) Each treated substrate was then rinsed with water at a flow rate of 1 L/min with a water temperature of 32 to 38° C. The rough surface (surface on which the personal care composition was applied) faced the flow of rinse water at a 45° angle, 5 to 10 cm from the faucet outlet for 15 seconds; (h) Each rinsed substrate was then placed in a clean tray with the treated surface facing up and left to dry for an hour before proceeding with an oil deposition analysis.

Oil Deposition Analysis

The mineral oil deposition on Vitro-Skin© advanced testing substrate was quantified by two dimensional gas chromatography mass spectrometry (2D-GC/MS) analysis.

Sample preparation: Each rinsed skin deposition sample (one piece of 4 cm×4 cm) was then placed in a 1 oz vial filled with 20 mL of hexane. Samples were then shaken for ~1.5 hours on a shaker. The solution phase in each vial was then filtered through a 0.2 μm nylon PTFE syringe filter prior to analysis by 2D-GC/MS.

2D-GC/MS condition: An Agilent 7890B GC equipped with a flame ionization detector (FID) and a 5977A mass selective detector (MSD) was used for the analysis of mineral oil. The GC conditions are listed below in TABLE 3.

TABLE 3

| | |
|---|---|
| Instrument | Agilent 7890B GC with 5977A MSD with Extractor EI source |
| Column: | First dimension: Agilent DB-17HT, 15 m × 0.25 mm, 0.15 μm film |
| | Second dimension: VF-WAXms, 30 m × 0.25 mm, 1.0 μm film |
| | Restrictor: Agilent 0.6 m × 0.1 mm ID fused silica |
| Injection volume | 1 μL |
| Inlet | Temperature: 240° C. |
| | Split ratio: 10:1 |
| | Carrier gas: Helium |
| Flow Programming | First dimension: 1.0 mL/min for 7.8 min, ramp to −1.0 mL/min at 99 mL/min, hold at −1.0 mL/min for 5.2 min (back flush step) |
| | Second dimension: 2.5 mL/min constant flow |
| Oven Temperature Programming: | 80° C. (1 min), 20° C./min to 250° C. (3.5 min). Total run time: 13 min |
| FID Parameters: | Temperature: 260° C. |
| | Air flow: 400 mL/min |
| | $H_2$ flow: 40 mL/min |
| | Makeup ($N_2$) flow: 25 mL/min |
| Heart-cutting event: | Cut windows: 7-7.07 min (C16) |
| MSD Parameters: | Transfer line temperature: 260° C. |
| | EI source temperature: 230° C. |
| | Quad temperature: 150° C. |
| | EM voltage: 1668 V |
| | Energy: 70 eV |
| | Gain factor: 5 |
| | SIM ion: m/z 71 (100 ms dwell time) and 85 (100 ms dwell time). Plot m/z 71 only. |

The external calibration was applied for obtaining the response factor of mineral oil (Lilac® highly refined mineral oil from Sonneborn, LLC). Mineral oil standards were prepared in hexane with the concentration range of 1 to 200 mg/L. Mineral oil contains a mixture of hydrocarbons exhibiting numerous peaks when analyzed by one dimensional GC. To quantify the amount of mineral oil deposited on the Vitro-Skin® advanced testing substrates, the most abundant hydrocarbon C16 peak was cut to the second dimension GC column and the signal for the C16 peak from the second dimension detector (MSD) was used for quantification.

The percent deposition of mineral oil was calculated using the equation below:

Deposition %=(((*W*×mineral *oil* wt %)/*v*)/*C*)

wherein Deposition % is the wt % of mineral oil from the applied formulation remaining on the Vitro-Skin® advanced testing substrate; wherein C is the concentration of mineral oil in the extraction solvent measured by 2D-GC/MS in mg/mL; wherein W is the weight of formulation applied onto the Vitro-Skin® advanced testing substrate in mg; wherein mineral oil wt % is the concentration of mineral oil in the formulation applied in wt %; and wherein v is the volume of hexane added into the formulation applied in mL. The results are provided in TABLE 4.

TABLE 4

| Personal Care Composition | Mineral oil wt % deposition |
|---|---|
| Comparative Example C1 | 15.09 |
| Comparative Example C2 | 10.38 |
| Example 1 | 18.60 |
| Example 2 | 26.32 |
| Example 3 | 27.47 |
| Example 4 | 24.80 |

We claim:

1. A personal care composition, comprising:
a vehicle;
a cosmetically acceptable oil; and
a cationic polymer comprising
   (a) 10 to 75 wt % of structural units of acrylamide monomer;
   (b) 20 to 80 wt % of structural units of N,N-dimethyl acrylamide monomer;
   (c) 5 to <25 wt % of structural units of monoethylenically unsaturated monocationic monomer of formula (I)

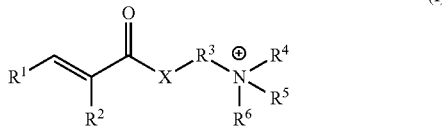

(I)

wherein $R^1$ is a —H or a —$CH_3$ group; wherein $R^2$ is a —H or a —$CH_3$ group;
wherein X is an —O— or a —N—; wherein $R^3$ is a —$C_{1-4}$ alkylene; wherein $R^4$, $R^5$ and $R^6$ are each independently a —H or a $C_{1-30}$ alkyl group; with the proviso that $R^4$ and $R^5$ are each a —H or a —$CH_3$ group and $R^6$ is a —$C_{5-30}$ alkyl group in 1 to 100 mol % of the structural units of unsaturated monomer of formula (I);
wherein the cationic polymer comprises >65 wt % of structural units of (a) and (b) combined; wherein the cationic polymer comprises <10 mol % of structural units of multiethylenically unsaturated cationic monomer; wherein the cationic polymer comprises <30 wt % of structural units of ester containing monomers; wherein the cationic polymer comprises <1 mol % of structural units of ethylenically unsaturated monomers containing a moiety selected from the group consisting of an epoxy, an anhydride, an imide, a lactone, a carboxylic acid, a sulfonic acid and an isocyanate;
wherein the cationic polymer comprises <0.1 mol % of structural units of a reactive siloxane; and
wherein the personal care composition comprises <0.05 wt % of water soluble, organic, ampholytic polymer conditioning agent.

2. The personal care composition of claim 1, wherein X is an —O—; and wherein $R^4$ and $R^5$ are each a —H or a —$CH_3$ group and $R^6$ is a —$C_{5-18}$ alkyl group in 25 to 100 mol % of the structural units of unsaturated monomer of formula (I).

3. The personal care composition of claim 1, wherein X is an —O—; and wherein at $R^4$ and $R^5$ are each a —H or a —$CH_3$ group and $R^6$ is a is a —$C_{5-2}$ alkyl group in 98 to 100 mol % of the structural units of unsaturated monomer of formula (I).

4. The personal care composition of claim 1, wherein the cosmetically acceptable oil is selected from the group consisting of mineral oil, petroleum jelly, sunflower oil, soybean oil, coconut oil, silicone oil and fragrance oil.

5. The personal care composition of claim 1, wherein the vehicle comprises water; wherein the personal care composition is an aqueous personal care composition.

6. The aqueous personal care composition of claim 5, further comprising at least one additional ingredient selected from the group consisting of an antimicrobial agent, a personal care cleaning surfactant, a rheology modifier, a soap, a colorant, pH adjusting agent, an antioxidant, a humectant, a wax, a foaming agent, an emulsifying agent, a colorant, a fragrance, a chelating agent, a preservative, a bleaching agent, a lubricating agent, a sensory modifier, a sunscreen additive, a vitamin, a protein/amino acid, a plant extract, a natural ingredient, a bioactive agent, an anti-aging agent, a penetrant, an anti-static agent, an anti-frizz agent, an antidandruff agent, a hair waving/straightening agent, a hair styling agent, an absorbent, a hard particle, a conditioning agent, a slippery agent, an opacifier, a pearlizing agent, a salt and mixtures thereof.

7. The aqueous personal care composition of claim 5, further comprising a personal care cleaning surfactant; wherein the aqueous personal care composition is a body wash formulation.

8. The body wash formulation of claim 7, wherein the personal care cleaning surfactant comprises a mixture of sodium laureth sulfate (SLES) and cocamidopropyl betaine; and wherein the cosmetically acceptable oil is selected from the group consisting of mineral oil, petroleum jelly, sunflower oil, soybean oil, coconut oil, silicone oil and fragrance oil.

9. A method of using a personal care composition, comprising:
providing a personal care composition according to claim 1; and
applying the personal care composition to at least one of skin and hair.

10. The personal care composition of claim 1, wherein X is an —O—; and wherein $R^4$ and $R^5$ are each a —H or a —$CH_3$ group and $R^6$ is a —$C_{5-8}$ alkyl group in 50 to 100 mol % of the structural units of unsaturated monomer of formula (I).

11. The personal care composition of claim 1, wherein X is an —O—; and wherein $R^4$ and $R^5$ are each a —H or a —$CH_3$ group and $R^6$ is a —$C_{5-8}$ alkyl group in 95 to 100 mol % of the structural units of unsaturated monomer of formula (I).

12. The personal care composition of claim 1, wherein X is an —O—; and wherein $R^4$ and $R^5$ are each a —H or a —$CH_3$ group and $R^6$ is a —$C_{5-8}$ alkyl group in 98 to 100 mol % of the structural units of unsaturated monomer of formula (I).

13. The personal care composition of claim 1, wherein X is an —O—; and wherein $R^4$ and $R^5$ are each —$CH_3$ group and $R^6$ is a —$C_{6-16}$ alkyl group in 98 to 100 mol % of the structural units of unsaturated monomer of formula (I).

14. The personal care composition of claim 11, wherein the cationic polymer comprises 5 to 20 weight percent of structural units of the monoethylenically unsaturated monocationic monomer of formula (I).

15. The personal care composition of claim 10 wherein the cationic polymer comprises 5 to 15 weight percent of structural units of the monoethylenically unsaturated monocationic monomer of formula (I).

16. The personal care composition of claim 10 wherein the cationic polymer comprises 5 to 12 weight percent of structural units of the monoethylenically unsaturated monocationic monomer of formula (I).

17. The method of claim 9 wherein the applying step is applying the personal care composition to the skin and the personal care composition is a body wash formulation, an exfoliating body wash formulation, a facial wash formulation, an exfoliating facial wash formulation, or a liquid hand soap.

18. The composition of claim 13 wherein $R^1$ is H, $R^2$ is methyl, and $R^3$ is ethylene.

19. The method of claim 9 wherein the personal care composition is applied to the skin.

20. A personal care composition, comprising:
a vehicle;
a cosmetically acceptable oil; and
a cationic polymer comprising
(a) 1 to 98 wt % of structural units of acrylamide monomer;
(b) 1 to 98 wt %) of structural units of N,N-dimethyl acrylamide monomer;
(c) 1 to <30 wt % of structural units of monoethylenically unsaturated monocationic monomer of formula (I)

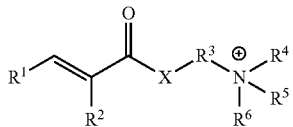 (I)

wherein R is a —H or a —$CH_3$ group; wherein $R^2$ is a —H or a —$CH_3$ group;

wherein X is an —O— or a —N—; wherein $R^3$ is a —$C_{1-4}$ alkylene; wherein $R^4$, $R^5$ and $R^6$ are each independently a —H or a $C_{1-30}$ alkyl group; with the proviso that $R^4$ and $R^5$ are each a —H or a —$CH_3$ group and $R^6$ is a —$C_{2-30}$ alkyl group in 1 to 100 mol % of the structural units of unsaturated monomer of formula (I);

wherein the cationic polymer comprises >65 wt % of structural units of (a) and (b) combined; wherein the cationic polymer comprises <10 mol % t of structural units of multiethylenically unsaturated cationic monomer; wherein the cationic polymer comprises <30 wt % of structural units of ester containing monomers; wherein the cationic polymer comprises <1 mol % of structural units of ethylenically unsaturated monomers containing a moiety selected from the group consisting of an epoxy, an anhydride, an imide, a lactone, a carboxylic acid, a sulfonic acid and an isocyanate;

wherein the cationic polymer comprises <0.1 mol % of structural units of a reactive siloxane; and wherein the personal care composition comprises <0.05 wt % of water soluble, organic, ampholytic polymer conditioning agent, wherein the composition provides an oil deposition percentage of at least 18.6%.

* * * * *